(12) United States Patent
Dahl

(10) Patent No.: US 9,085,513 B2
(45) Date of Patent: Jul. 21, 2015

(54) CO-PRODUCTION OF METHANOL AND UREA

(71) Applicant: Haldor Topsøe A/S, Kgs. Lyngby (DK)

(72) Inventor: Per Juul Dahl, Vedbæk (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/366,293

(22) PCT Filed: Dec. 21, 2012

(86) PCT No.: PCT/EP2012/076667
§ 371 (c)(1),
(2) Date: Jun. 18, 2014

(87) PCT Pub. No.: WO2013/102589
PCT Pub. Date: Jul. 11, 2013

(65) Prior Publication Data
US 2014/0357736 A1    Dec. 4, 2014

(30) Foreign Application Priority Data

Jan. 4, 2012 (DK) .............................. 2012 00008

(51) Int. Cl.
| | | |
|---|---|---|
| C07C 273/10 | (2006.01) |
| C01B 3/02 | (2006.01) |
| C01B 3/38 | (2006.01) |
| C07C 29/151 | (2006.01) |
| C07C 273/04 | (2006.01) |
| C01B 3/48 | (2006.01) |
| C01C 1/04 | (2006.01) |

(52) U.S. Cl.
CPC ............... *C07C 273/10* (2013.01); *C01B 3/025* (2013.01); *C01B 3/382* (2013.01); *C01B 3/48* (2013.01); *C01C 1/0488* (2013.01); *C07C 29/1518* (2013.01); *C07C 273/04* (2013.01); *C01B 2203/025* (2013.01); *C01B 2203/0233* (2013.01); *C01B 2203/0238* (2013.01); *C01B 2203/0244* (2013.01); *C01B 2203/0283* (2013.01); *C01B 2203/0415* (2013.01); *C01B 2203/0475* (2013.01); *C01B 2203/061* (2013.01); *C01B 2203/068* (2013.01); *C01B 2203/1235* (2013.01); *C01B 2203/82* (2013.01)

(58) Field of Classification Search
None
See application file for complete search history.

(56) References Cited

U.S. PATENT DOCUMENTS

2002/0098132 A1    7/2002  Vidalin
2007/0299144 A1 *  12/2007 Davey et al. .................. 518/703

FOREIGN PATENT DOCUMENTS

WO    WO 2011/020618 A1    2/2011

* cited by examiner

*Primary Examiner* — Sudhakar Katakam
(74) *Attorney, Agent, or Firm* — Dickstein Shapiro LLP

(57) ABSTRACT

Process for the co-production of methanol and urea from a hydrocarbon feed without venting large amounts of carbon dioxide to the atmosphere.

10 Claims, No Drawings

CO-PRODUCTION OF METHANOL AND UREA

The present invention relates to a process for the co-production of methanol and urea from a hydrocarbon feed. More particularly the invention is concerned with a sequential and once-through (single pass) process for the production of methanol and urea product from a hydrocarbon containing feed stock by means of primary and secondary reforming, intermediary methanol and ammonia formation and conversion of the ammonia to urea product in a single process train, with a much reduced production of excess of carbon dioxide and hydrogen.

Production of urea by conversion of ammonia and carbon dioxide is a well known process and conventionally employed in the industry.

It is further known from US patent application No. 2010/0133472 to co-produce methanol and ammonia from synthesis gas with reduced production of excess of carbon dioxide and hydrogen.

It is the general object of the invention to provide a process for co-producing methanol and urea with much reduced production of excess of carbon dioxide and hydrogen from a hydrocarbon feed stock.

The term "much reduced production of excess of carbon dioxide and hydrogen" shall be understood in such a manner that conversion of the hydrocarbon feed stock to synthesis gas is performed at conditions to provide a substantially stoichiometric synthesis gas for the production of methanol and urea, resulting in emission of carbon dioxide and hydrogen only as required for purging of inert gases from the co-production of methanol and urea.

The general object of the invention is achieved when performing the production of synthesis gas in a combined steam and carbon dioxide primary hydrocarbon reforming step and a secondary reforming secondary step with oxygen enriched air.

Accordingly, the invention provides a process for co-producing methanol and urea from a hydrocarbon feedstock comprising the sequential steps of:

(a) producing a synthesis gas containing hydrogen, carbon monoxide and dioxide and nitrogen by steam reforming the hydrocarbon feedstock in a primary reforming stage and subsequently in a secondary reforming stage;

(b) subjecting the synthesis gas from step (a) to a partial water gas shift;

(c) removing at least part of the carbon dioxide from the synthesis gas from step (b);

(d) catalytically converting the carbon monoxide, carbon dioxide and hydrogen of the synthesis gas from step (c) in a once-through methanol synthesis stage and withdrawing an effluent containing methanol and a gaseous effluent containing nitrogen, hydrogen and unconverted carbon monoxide and carbon dioxide;

(e) subjecting the gaseous effluent from step (d) to catalytic methanation to remove the unconverted carbon monoxide and carbon dioxide;

(f) catalytically converting the nitrogen and hydrogen in the gaseous effluent from step (e) in an ammonia synthesis stage and withdrawing an effluent containing ammonia; and (g) passing at least part of the ammonia containing effluent to an urea synthesis stage and converting the ammonia in the effluent to urea product by reaction with at least part of the carbon dioxide being removed from the synthesis gas in step (c), wherein a part of the carbon dioxide obtained in step (c) is recycled to the primary reforming stage in step (a), and/or wherein the secondary reforming stage in step (a) is operated with oxygen enriched air.

As used herein the term "partial water gas shift of the synthesis gas" means that a part of synthesis gas is bypassed the water gas shift reaction and combined with the shifted synthesis gas after the reaction.

As further used herein the term "primary reforming stage" means reforming being conducted in a conventional steam methane reformer (SMR), i.e. tubular reformer with the heat required for the endothermic reforming being provided by radiation heat from burners, such as burners arranged along the walls of the tubular reformer.

As also used herein the term "secondary reforming stage" means reforming being conducted in an autothermal reformer or catalytic partial oxidation reactor.

As further used herein, the term "once-through methanol synthesis stage" means that methanol is produced in at least one catalytic reactor operating in a single pass configuration, i.e. without significant recirculation (not more than 5%) of the volume flow of any gas produced in the methanol synthesis back to the at least one methanol reactor of the methanol synthesis stage, particularly the gas effluent containing hydrogen and unconverted carbon oxides.

Suitable hydrocarbon feed stocks for use in the invention include methane, natural gas, naphtha and higher hydrocarbons.

Preferably the hydrocarbon feedstock comprises methane, for instance in the form of natural gas, liquefied natural gas (LNG) or substitute natural gas (SNG).

When employing naphtha and higher hydrocarbons, it is preferred to subject these feed stocks to a prereforming step prior to the primary reforming stage. However, prereforming can be employed for all types of hydrocarbon feed stock.

By the invention we make direct use of the reactions governing reforming, methanol synthesis, ammonia synthesis and urea synthesis so that methanol and urea can be co-produced without venting carbon dioxide being removed from the secondary reformed synthesis gas.

By the process according to the invention the amount of carbon dioxide and carbon monoxide in the synthesis gas from step (b), minus the amount of carbon dioxide recycle from step(c) to step(a), fulfils the stoichiometric required amount in the methanol synthesis reaction and the urea reaction:

$$CO+2H_2=CH_3OH$$

$$CO_2+3H_2=CH_3OH+H_2O$$

$$2NH_3+CO_2=(NH_2)_2CO+H_2O$$

At the same time the amount of hydrogen and nitrogen in the synthesis gas from step (a) matches the stoichiometric required amounts in both the above methanol synthesis reactions and the ammonia synthesis:

$$2N_2+3H_2=2NH_3$$

This means that the molar content of $H_2$, $CO$, $CO_2$ in the synthesis gas from step (b) shall fulfil the relation:

$$M(H_2)=3*M(N_2)+2*M(CO)+3*(M(CO_2)-M(N_2)-REC)$$

where REC is the molar $CO_2$ recycle flow from step (c) to step (a).

This is obtained, when controlling the primary steam reforming reactions:

$$CH_4 + H_2O = CO + 3H_2;\text{ and}$$

$$CH_4 + 2H_2O = CO_2 + 4H_2$$

and/or the partial oxidation with oxygen enriched air in the subsequent secondary steam reforming:

$$CH_4 + \tfrac{1}{2}O_2 = CO + 2H_2$$

and the water-gas-shift reaction:

$$H_2O + CO = CO_2 + H_2$$

To maintain the required amounts of carbon monoxide, carbon dioxide and hydrogen in the final synthesis gas, a controlled amount of carbon dioxide removed from the gas may be recycled to the primary reforming stage to suppress the shift reaction in order to avoid a production of hydrogen and carbon dioxide in excess of the required amounts to be used in the methanol, ammonia and urea synthesis.

The secondary reforming is conducted in a secondary reformer or autothermal reformer with oxygen enriched air in order to provide for the required amount of nitrogen for the ammonia synthesis and the required amount of carbon monoxide, carbon dioxide and hydrogen for the methanol synthesis together with required amount of carbon dioxide necessary for carbon dioxide recycle to the primary reformer and the conversion of ammonia to urea.

Final control of the carbon monoxide/carbon dioxide ratio to meet the required amount of nitrogen, carbon monoxide, carbon dioxide and hydrogen for the methanol and ammonia synthesis together with required amount of carbon dioxide necessary for carbon dioxide recycle to the primary reformer and the conversion of ammonia to urea, is obtained by subjecting part of the synthesis gas to the water gas shift reaction prior to the removal of carbon dioxide in step (c).

The final synthesis gas is by the above measures adjusted to contain carbon monoxide, carbon dioxide, hydrogen and nitrogen in a molar ratio substantially complying to the stoichiometric amounts in the methanol synthesis and in the ammonia synthesis and to provide the necessary amount of carbon dioxide for use in the urea synthesis and optionally for use in the primary reforming stage.

Thus, in a preferred embodiment of the invention the molar content of H2, CO, CO2, and N2 in the synthesis gas from the partial shift in step (b) fullfill the following relation I, within 10% accuracy:

$$M(H_2) = 3*M(N_2) + 2*M(CO) + 3*(M(CO_2) - M(N_2) - REC) \qquad \text{I}$$

where REC is the molar $CO_2$ recycle flow from step (c) to step (a).

The relation I is obtained by recycling carbon dioxide from step (c) to the primary reforming stage in step (a) and/or by operating the secondary reforming stage in step (a) with oxygen enriched air and/or by partial shift of the synthesis gas from step (a).

The process of the present invention is environmentally friendly because there are no emissions to the surroundings of the $CO_2$ removed from secondary reformed synthesis gas. Practically all carbon monoxide (and carbon dioxide) produced in the process is used for methanol and the urea synthesis, beside small amounts of carbon dioxide which are vented to the atmosphere in purge gas.

Removal of carbon dioxide from the secondary reformed synthesis gas may be performed by any conventional means in a physical or chemical wash as known in the art.

Preferably, carbon dioxide is removed by the known Benefield process, which allows easy recovery of absorbed carbon dioxide for use in the urea synthesis and optionally for recycle to the primary reforming stage, as discussed above.

The methanol synthesis stage is preferably conducted by conventional means by passing the synthesis gas at high pressure and temperatures, such as 60-150 bar and 150-300° C. through at least one methanol reactor containing at least one fixed bed of methanol catalyst. A particularly preferred methanol reactor is a fixed bed reactor cooled by a suitable cooling agent such as boiling water, e.g. boiling water reactor (BWR). In a specific embodiment the methanol synthesis stage in step (d) is conducted by passing the synthesis gas through a series of one or more boiling water reactors and subsequently through an adiabatic fixed bed reactor. Preferably the one or more boiling water reactor is in the form of a single reactor of the condensing methanol type which comprises within a common shell a fixed bed of methanol catalyst particles and cooling means adapted to indirectly cooling the methanol synthesis gas with a cooling agent, and which preferably operates at pressures above 90 bar and below 150 bar, more preferably above 110 bar and below 130 bar, as described in our DK patent applications PA 2008 00261 and PA 2008 00260 filed 25 Feb. 2008. The use of a methanol reactor according to these applications enables operation at pressures much higher than conventional boiling reactors which typically are about 80 to 90 bar. In addition it enables the use of a single reactor rather than two conventional boiling water reactors, thereby significantly reducing plant costs. Furthermore, since the operating pressure in the methanol synthesis stage can be kept as high as about 120 bar or even higher there are significant savings in terms of equipment size and overall investment costs as methanol synthesis is favoured at high pressures.

Accordingly, the invention enables the operation of the methanol and ammonia synthesis section at similar operating pressures, for instance 130 bar, which implies a simplified process with significant savings in size of equipment as mentioned above. Yet it is also possible to operate at two different operating pressures, for instance 80-90 bar in the methanol synthesis stage and 130 bar in the ammonia synthesis stage, which implies energy savings in the methanol synthesis stage.

In step (d) the effluent containing methanol is preferably a liquid effluent. This effluent is obtained by cooling and condensation of the synthesis gas from the methanol reactors. Accordingly the process of the invention may further comprise cooling the synthesis gas withdrawn from each methanol reactor to condense methanol and passing the gas through a separator, withdrawing a bottom fraction from the separator containing the raw methanol, withdrawing an over-head fraction containing synthesis gas which is passed to the subsequent methanol reactor, and forming a single liquid effluent containing methanol by combining the bottom fractions of the separators of each reactor containing the raw methanol.

It would be understood that the term "methanol reactor" as used herein encompasses adiabatic fixed bed reactors and cooled reactors such as boiling water reactors and reactors of the condensing-methanol type which comprises within a common shell a fixed bed of methanol catalyst particles and cooling means adapted to indirectly cooling the methanol synthesis gas with a cooling agent adiabatic fixed bed reactors.

In step (e) the catalytic methanation stage for conversion of carbon monoxide to methane is conducted in at least one methanation reactor, which is preferably an adiabatic reactor containing a fixed bed of methanation catalyst.

In step (f) the ammonia synthesis gas from the methanation stage containing the correct proportion of hydrogen and nitrogen ($H_2:N_2$ molar ratio of 3:1) is optionally passed through a compressor to obtain the required ammonia synthesis pressure, such as 120 to 200 bar, preferably about 130 bar. Ammonia is then produced in a conventional manner by means of an ammonia synthesis loop comprising at least one ammonia converter containing at least one fixed bed of ammonia catalyst, with interbed cooling. Ammonia may be recovered from the effluent containing ammonia as liquid ammonia by condensation and subsequent separation. Preferably, an off-gas stream containing hydrogen, nitrogen and methane is withdrawn from the ammonia synthesis stage, as also is a hydrogen-rich stream (>90 vol % $H_2$). These streams may for instance stem from a purge gas recovery unit. Preferably, this hydrogen stream is added to the methanol synthesis stage (step (c)), for instance by combining with the methanol synthesis gas. The recycle of this hydrogen-rich stream enables a higher efficiency in the process as useful hydrogen is utilised in the methanol synthesis and subsequent ammonia synthesis rather than simply being used as fuel.

In order to improve the energy efficiency of the process the off-gas stream containing hydrogen, nitrogen and methane of step (e) is returned to step (a), i.e. it is returned as off-gas fuel to the reforming section of the plant, specifically to the primary reforming stage.

The ammonia being withdrawn from the ammonia synthesis is then converted to the urea product by reaction with carbon dioxide recovered from step (c) as described above.

By the invention part of the ammonia can be withdrawn as an ammonia product which alters relation I as follows:

$$M(H_2)=3*M(N_2)+2*M(CO)+3*(M(CO_2)-M(N_2)+2*P-REC) \quad \text{II}$$

where P is the molar ammonia product from step (f).

The invention claimed is:

1. Process for co-producing methanol and urea from a hydrocarbon feedstock comprising the sequential steps of:
    (a) producing a synthesis gas containing hydrogen, carbon monoxide and dioxide and nitrogen by steam reforming the hydrocarbon feedstock in a primary reforming stage and subsequently in a secondary reforming stage;
    (b) subjecting the synthesis gas from step (a) to a partial water gas shift;
    (c) removing at least part of the carbon dioxide from the synthesis gas from step (b);
    (d) catalytically converting the carbon monoxide, carbon dioxide and hydrogen of the synthesis gas from step (c) in a once through methanol synthesis stage and withdrawing an effluent containing methanol and a gaseous effluent containing nitrogen, hydrogen and unconverted carbon monoxide and carbon dioxide;
    (e) subjecting the gaseous effluent from step (d) to catalytic methanation to remove the unconverted carbon monoxide and carbon dioxide;
    (f) catalytically converting the nitrogen and hydrogen in the gaseous effluent from step (e) in an ammonia synthesis stage and withdrawing an effluent containing ammonia; and
    (g) passing at least part of the ammonia containing effluent to an urea synthesis stage and converting the ammonia in the effluent to urea product by reaction with at least part of the carbon dioxide being removed from the synthesis gas in step (c),
    wherein the secondary reforming stage in step (a) is operated with oxygen enriched air.

2. Process according to claim 1, wherein the molar content of $H_2$, CO, $CO_2$, and 2 in the synthesis gas from the partial shift in step (b) fulfils the following relation I, within 10% accuracy:

$$M(H_2)=3*M(N_2)+2*M(CO)+3*(M(CO_2)-M(N_2)-REC) \quad \text{I}$$

where REC is the molar CO, recycle flow from step (c) to step (a), and M is the molar content.

3. Process according to claim 1 wherein the hydrocarbon feedstock is natural gas, substitute natural gas (SNG), naphtha and higher hydrocarbons.

4. Process according to claim 1, wherein the carbon dioxide is recycled to the primary reforming stage in step (a) in an amount to obtain a molar ratio of carbon dioxide to methane of 0.0 to 0.43.

5. Process according to claim 1, wherein the secondary reforming step is performed with the oxygen enriched air and wherein the oxygen enriched air contains ambient content of oxygen up to 99.5 vol % pure oxygen.

6. Process according to claim 1, wherein the methanol synthesis stage in step (d) is conducted by passing the synthesis gas through a series of one or more boiling water reactors and subsequently through an adiabatic fixed bed reactor.

7. Process according to claim 6, wherein the one or more boiling water reactor is in the form of a single reactor of the condensing methanol type which comprises within a common shell a fixed bed of methanol catalyst particles and cooling means adapted to indirectly cooling the methanol synthesis gas with a cooling agent.

8. Process according to claim 6, further comprising cooling the synthesis gas withdrawn from each methanol reactor to condense methanol and passing the gas through a separator, withdrawing a bottom fraction from the separator containing the raw methanol, withdrawing an overhead fraction containing synthesis gas which is passed to the subsequent methanol, and forming a single liquid effluent containing methanol by combining the bottom fractions of the separators of each reactor containing the raw methanol.

9. Process according to claim 1, wherein an off-gas stream containing hydrogen, nitrogen and methane is employed as fuel for heating the primary reforming stage in step (a).

10. Process according to claim 1, wherein the hydrocarbon feed stock is subjected to pre-reforming upstream of step (a).

* * * * *